United States Patent [19]

Don Michael et al.

[11] Patent Number: 4,706,688
[45] Date of Patent: Nov. 17, 1987

[54] NON-INVASIVE CARDIAC DEVICE

[76] Inventors: T. Anthony Don Michael, 2108 Truxtun Ave., Bakersfield, Calif. 93301; Edward H. Lambert, 44 Gunton Drive, Lowestoft Suffolk, NR 32 4QB, United Kingdom

[21] Appl. No.: 545,535

[22] Filed: Oct. 26, 1983

Related U.S. Application Data

[63] Continuation of Ser. No. 264,961, May 18, 1981, abandoned.

[51] Int. Cl.⁴ .............................................. A61B 1/04
[52] U.S. Cl. ............................. 128/785; 128/419 D; 128/642
[58] Field of Search .................. 128/784–786, 128/419 D, 642, 715

[56] References Cited

U.S. PATENT DOCUMENTS

| 4,088,138 | 5/1978 | Diack et al. | 128/419 D |
| 4,198,963 | 4/1980 | Barkalow et al. | 128/642 |
| 4,304,239 | 12/1981 | Perlin | 128/786 |

FOREIGN PATENT DOCUMENTS 133400  1/1979  German Democratic Rep. ................ 128/786

Primary Examiner—William E. Kamm
Attorney, Agent, or Firm—Spensley Horn Jubas & Lubitz

[57] ABSTRACT

A non-invasive cardiac device is disclosed which can be inserted through the esophagus and into the gastroesophageal junction region. Once in place, a selected portion of the device is urged adjacent the cardiac region. The device comprises an elongated conduit having a series of electrodes for sensing or recording electrical signals. A first means for positioning the device adjacent the gastroesophageal region is located adjacent a first end of the device. The device further includes a second means for positioning the device in the esophagus such that at least some of the electrodes are urged adjacent the cardiac region.

5 Claims, 3 Drawing Figures

NON-INVASIVE CARDIAC DEVICE

This is a continuation of application Ser. No. 264,961, filed on May 18, 1981, now abandoned.

BACKGROUND OF THE INVENTION

1. Field of the Invention.

The present invention relates to the field of medical devices, and more specifically, to a non-invasive cardiac device which can be used in the treatment of many heart ailments.

2. Prior Art.

The treatment of heart ailments has evolved many medical devices. For example, in instances where a person is suffering from irregular heart beats, it is sometimes necessary to "defibrillate" the heart by means of high voltage electric paddles. While these have a number of disadvantages, because a life or death situation is usually involved, they are extensively used. Other medical devices also associated with the heart, include surgically inserted pacemakers. Such pacemakers are used, at least in one embodiment, to encourage the heart to beat in a predetermined manner. Yet other medical devices include the well known ECG machines which, while not used directly in the treatment of the patient, are used to determine whether a patient's heart is beating properly or whether there are arrhythmias.

Thus, there exists a plurality of heart-related devices which serve different needs of the patient. These devices tend to be relatively complex, in some situations even requiring surgery before they can be used, are expensive to make, and can be dangerous both to the patient as well as to medical personnel. There has thus existed for a long time a need for a device which can perform a plurality of different functions which would not suffer from the shortcomings discussed hereinabove. That is, a device which would not require the type of surgery associated with the insertion of present-day pacemakers, but which could still perform a pace-making function. Likewise, there is a need for a device which could be used to "shock" the heart so as to alleviate an arrhythmia, but not suffer from the dangers of present-day electric paddles. There is also a need for a device which would permit a more exacting determination of a patient's ECG. More cogently, this device would be capable of insertion and function in an emergency wherein pacing, defibrillation or scanning the electrogram is needed. Other existing devices do not provide for emergency pacing in this manner, nor do they combine all three functions.

These and other advantages are achieved by the device of the present invention.

BRIEF SUMMARY OF THE INVENTION

The present invention relates to a non-invasive cardiac electrode device. The device is designed to be inserted through the esophagus and into the gastro-esophageal junction region of a human. Once properly inserted a selected portion of the device is urged against the cardiac region. The device comprises an elongated conduit having a series of band-like contacts disposed along the length thereof. A first balloon cuff is located adjacent the distal end of the conduit and can be selectively expanded. In operation, after the device is inserted, the first cuff is expanded so as to position the device such that the distal end of the conduit is adjacent the gastroesophageal junction. The device also includes a second balloon cuff located approximately midway along the length of the conduit. The second balloon cuff is expanded such that the electrodes are urged against the esophagus adjacent the cardiac region. Depending on patient's needs, the device can be operated to achieve atrial pacing, ventricular pacing, atrio-ventricular pacing, defibrillation and/or viewing of the electrogram. These and other objectives will be discussed in greater detail hereinbelow.

The novel features which are believed to be characteristic of the invention, both as to its organization and method of operation, together with further objectives and advantages thereof will be better understood from the following description considered in connection with the accompanying drawings in which the presently preferred embodiment of the invention is illustrated by way of example. It is to be expressly understood, however, the drawings are for the purpose of illustration and description only, and are not intended as a definition of the limits of the invention.

DETAILED DESCRIPTION OF THE INVENTION

Figure 1:
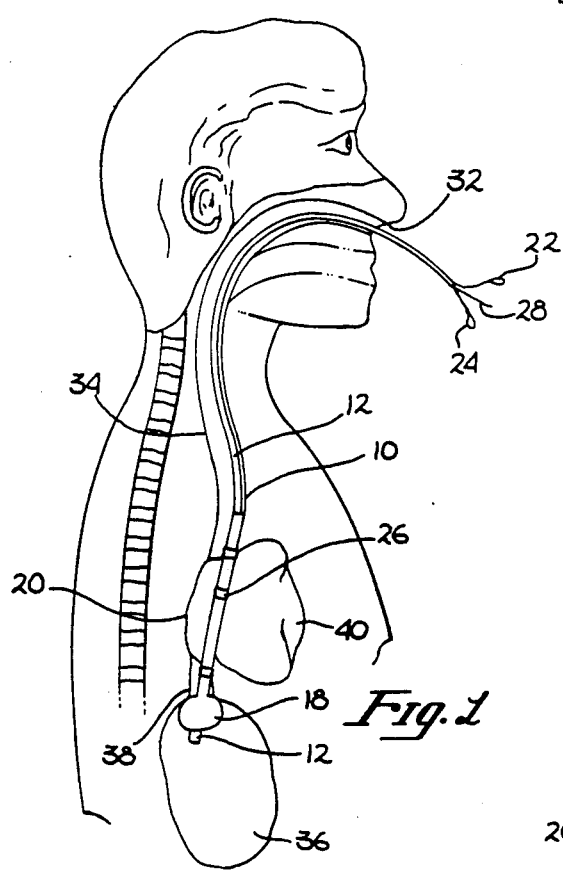
FIG. 1 is a front view showing the device of the present invention as it would be inserted into a human.
Figure 2:
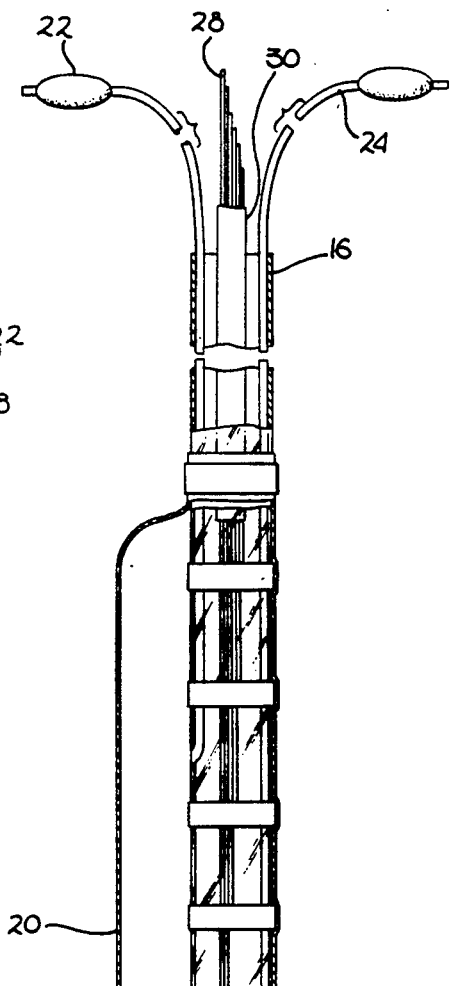
FIG. 2 is a front cut-away view of the device of the present invention showing the various elements thereof.

Referring to FIGS. 1 and 2, there is shown the device 10 of the present invention. The device 10 comprises an elongated, generally flexible plastic conduit 12 which has a first distal end 14 and a second proximal end 16. A first balloon cuff 18 is disposed adjacent distal end 14 and, in the preferred embodiment, comprises a readily expandable plastic member. A second balloon cuff 20 is disposed along the length of conduit 12 in a predetermined location. Second balloon cuff 20 can also be selectively expanded so as to position the device as discussed in greater detail hereinbelow. Cuffs 18 and 20 are in flow communication with airway members 22 and 24, respectively. These airway members preferably embedded in the conduit 12, are used to supply a fluid, usually air, to cuffs 18 and 20 so as to position the device 10 in a selected position along the length of an esophagus. For a typical human, the device 10 is made of a sufficient length such that metal band electrodes 26, disposed along the length of conduit 12, can be selectively positioned adjacent the cardiac region. In the preferred embodiment, the conduit 12 is approximately 40 centimeters long with cuff 18 being located approximately 2 centimeters from the distal end 14. The electrodes 26 are located such that they are approximately 30–40 cm from the proximal end 16. When end 16 is located adjacent the nares, this distance locates the electrodes 26 adjacent the heart. Alternatively, if the device 10 is to be used with end 16 adjacent the incisors, the electrodes 26 are located approximately 40–50 cm from end 16. Again, this helps insure that the electrodes 26 are positioned near the heart.

Connected to the electrodes 26 are wires 28, which are preferably embedded in wall 30 of the conduit 12. In this manner, electrical signals can be transferred to and received from the heart 40 via the electrodes 26.

Figure 3:
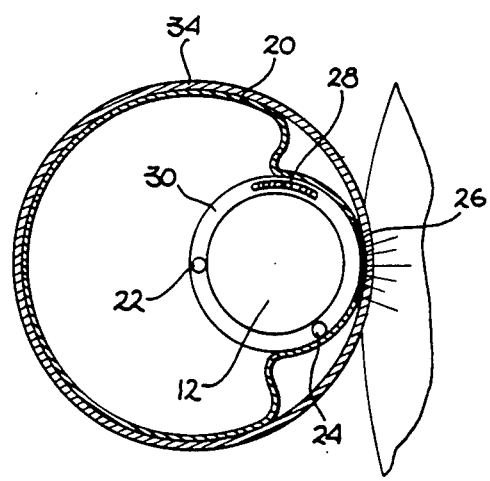
FIG. 3 shows the placement of the device of the present invention during operation.

Referring now specifically to FIGS. 2 and 3, one can see how the device 10 is inserted into the esophagus 34 of a patient. More specifically, in the preferred embodiment, the device 10 is inserted through the nasal region 32, through the esophagus 34 and into the stomach 36. Once the device 10 has been inserted, fluid is caused to flow along airway 24 such that cuff 18 expands. The purpose of cuff 18 is to locate the gastroesophageal junction just proximate to the cuff 18. In this manner, proper placement of the electrodes 26 is achieved. Next, the second balloon cuff 20 is expanded by means of airway 22. Cuff 20 is located posterior to the heart region 40 such that when it is expanded, at least some of the electrodes 26 abut against the esophagus 34 adjacent the heart 40. Balloon cuff 20 also achieves proper rotational, i.e., axial placement of the conduit 12 and electrodes 26 in the esophagus 34. Wires 28 can then be attached to an exterior pacemaker battery system for arterial pacing or ventricular pacing. In another embodiment, wires 28 could be connected to an ECG machine. Because electrodes 26 are extremely close to the heart 40, very accurate information can be obtained.

While the device 10 described above has been inserted through the nasal region 32, it can also be inserted through the mouth in a conscious or unconscious patient. During use, it may be necessary to remove the gastric contents which can be aspirated. Thus, conduit 12 is of a sufficient diameter to permit the passage of various gastric contents therethrough. To ensure there is no blockage of the gastroesophageal junction 38, once the device is properly positioned by means of first balloon cuff 18, such cuff 18 can be deflated.

By the use of the present invention, a trained paramedic or doctor can insert the device 10 within or outside of a hospital setting as part of other resuscitative equipment. In this manner the device 10 can achieve a number of advantages; to wit: 1. enables slower heart beats which are common in the initial stages of myocardial infarction to be optimized without the use of Atropine which has variable effects; 2. helps prevent malignant arrhythmias; 3. enables the treatment of atrio-ventricular block; 4. enables the analysis of rhythms through the esophagus; and 5. enables defibrillation to be carried out using small current strengths without delay and without interfering with the conduct of normal CPR.

It should be understood that while the preferred embodiment described herein has shown certain configurations, other changes can be made without departing from the spirit and scope of the present invention. For example, the present invention contemplates a generally cylindrical conduit 12 made out of plastic or similar material. In some instances, a shape other than cylindrical, i.e., oblong or the like, may also be used. With respect to contact 26, the present preferred embodiment contemplates the use of generally cylindrical bands of metal which are circumferentially disposed about conduit 12. In alternate embodiments, electrodes 26 may be disposed within the conduit and may have a cylindrical or other configuration. This invention, therefore, is not to be limited to that which is specifically disclosed and shown above.

We claim:

1. A non-invasive cardiac device which may be inserted through the esophagus and into the gastroesophageal junction region and a selected portion urged adjacent the cardiac region for internal stimulation, pacing, and monitoring, comprising:
    an elongated conduit having a series of electrodes disposed thereon along its length so as to be adjacent the cardiac region when the device is in position in the esophagus;
    first locating means for positioning said electrodes adjacent the cardiac region and a distal end of said device adjacent said gastroesophageal region, said first locating means being joined to said conduit at the conduit distal end; and
    second locating means for positioning said device in said esophagus joined to the conduit and extending outwardly therefrom with at least some of said electrodes in abutting contact with the cardiac region.

2. A non-invasive cardiac device according to claim 1 wherein said first and second locating means each comprises expandable balloon-like members which selectively inflatable to position the device in the esophagus.

3. A non-invasive cardiac device according to claim 2 including third locating means, joined to the first and second locating means and operable from a position exterior said esophagus, for supplying said first and second locating means with a fluid.

4. A non-invasive cardiac device according to claim 1 including an external measurement device and means for electrically coupling said electrodes to the external measurement device.

5. A non-invasive cardiac device according to claim 1 wherein said electrodes are conductive, generally circular bands.

* * * * *